United States Patent [19]

Colombotto et al.

[11] Patent Number: 4,584,476
[45] Date of Patent: Apr. 22, 1986

[54] DEVICE FOR THE NON-DESTRUCTIVE TESTING OF THE INTERNAL STRESS STATE OF HEAT TEMPERED PLATE GLASS

[75] Inventors: Amedeo Colombotto, Chieti; Ernesto Della Sala; Luciano Biasutti, both of Vasto, all of Italy

[73] Assignee: SOCIETA ITALIANA VETRO SIV S.p.A., Vasto, Italy

[21] Appl. No.: 534,627

[22] Filed: Sep. 19, 1983

[30] Foreign Application Priority Data

Sep. 21, 1982 [IT] Italy ............................ 49143 A/82

[51] Int. Cl.⁴ ..................... G01N 21/21; G01L 1/24
[52] U.S. Cl. ................................. 250/338; 250/341; 356/35
[58] Field of Search ............... 250/358.1, 341, 338 R; 356/370, 364, 33, 35, 366; 73/800

[56] References Cited

U.S. PATENT DOCUMENTS

| | | | |
|---|---|---|---|
| 1,681,991 | 8/1928 | Littleton, Jr. | 250/341 |
| 3,589,812 | 6/1971 | Robert et al. | 356/33 |
| 3,818,339 | 6/1974 | Black | 324/140 R |

FOREIGN PATENT DOCUMENTS

| | | | |
|---|---|---|---|
| 104743 | 8/1980 | Japan | 356/364 |
| 830313 | 3/1960 | United Kingdom | 73/800 |
| 1018002 | 9/1963 | United Kingdom . | |

*Primary Examiner*—Alfred E. Smith
*Assistant Examiner*—Constantine Hannaher
*Attorney, Agent, or Firm*—Browdy and Neimark

[57] ABSTRACT

The internal stress state of a plate of heat tempered plate glass is tested by means of a device which uses a source of polarized monochromatic infrared radiation. This radiation passes through the glass in a point, and the variation of the polarization state is determined by means of an analyzer with the polarization axis at 90° with respect to the polarizing filter.

10 Claims, 2 Drawing Figures

DEVICE FOR THE NON-DESTRUCTIVE TESTING OF THE INTERNAL STRESS STATE OF HEAT TEMPERED PLATE GLASS

The present invention refers to a device for measuring the mechanical stress in a transparent object, in particular heat tempered glass.

Current state of the art measurement methods involve analysis of the internal stress state by measuring the relative delay $\delta$ between the two components of polarized light into which electromagnetic radiation is divided when it passes through stressed transparent material.

This relative delay $\delta$ can be directly correlated to the internal stress state of the test material according to Maxwell's theory.

DESCRIPTION OF THE PRIOR ART

Typical applications of these methods can be found in the literature and are widely documented.

An article by GARDON, BAYMA and WARNICK in Experimental Mechanics, November 1966, entitled 'A recording photoelastic stress meter' describes a method and a device for measuring the mechanical stress in tempered glass, using a Babinet type compensation technique in which the quantitative measurement of the delay depends on the determination by the operator of the fringe order. Therefore, when the delay is greater than the wavelength of the impinging radiation, it is necessary to establish how many multiples (fringes) of the wavelength should be added to the instrumentally determined value.

This makes it impossible to automate the instrument, except for the case of low stress (<40 MPa) typical for example of annealed glass (float glass, etc.), and excludes that of tempered glass.

Therefore, the measurement method is no longer objective since cases of high stress involve the evaluation of the interference order by means of subjective evaluation of the colors of the interference fringe.

The precision of the method also decreases, since determining the color effects necessary for evaluating the interference order prevents the use of monochromatic light, with consequent loss of resolution and precison, even for low stresses.

U.S. Pat. No. 3,589,812 describes a method for measuring the delay $\delta$ by means of technique for analyzing the polarization which leads to a one point response, variable in intensity according to a sinusoidal type law. This response is correlated mathematically with the delay $\delta$.

A series of simplifying hypothese allows the value $\delta$ to be determined numerically from the intensity measurement.

The U.S. Pat. No. 3,589,812 cited above involves refinement of the experimental techniques to make the measurement as reliabe as possible. This measurement is effected using a traditional type light source. However, the problems related to the precision of the instrument for high stress values still remain. For transmission measurements in particular, evaluation of the interference order remains indispensable.

In practice, in the current state of the art, the most simple and reliable system for testing the stress state of tempered glass consists of breaking the glass and examining the fracture configuration, so as to have statistical control during production of tempered plate glass.

SUMMARY OF THE INVENTION

The aim of the present invention is to provide a device for the non-destructive testing of heat tempered plate glass which combines high intrinsic precision with the possiblitity of completely automated testing.

A common characteristic of the technology for tempering glass by means of heat exchange is to place high compression values along the edges of the plate, which can be correlated, as a function of the specific characteristics of the technology used, with the state of tempering of the plate itself. The presence of this compression can readily be seen by means of polariscopy, and may be quantified by counting and evaluating the interference fringes.

Typical values of this compression state of the tempered glass range from 40 to 70 MPa, that is above the values for which the GARDON method can be used, without requiring counting the fringes.

For the type of measurement in question, the method described in the U.S. patent cited above presents the same difficulties.

From the preceding discussion, it is obvious that previous systems inherently involved the use of wavelengths of light in the visible range which was also non-monochromatic, in order to measure the relative delay $\delta$ mentioned above.

According to the present invention, an apparatus is provided which uses monochromatic light with a wavelength in the near infrared in order to measure the quantity of radiation passing through the glass plate, polarized in a polarizing plane.

It has been surprisingly discovered that even the stress state in one point of a heat tempered glass plate can be determined by means of a simple measurement of the variation of the polarization of the radiation passing through said plate, when infrared radiation is used.

More precisely, the polarization component is measured of the radiation coming from a point of the plate at 90° with respect to the polarization plane of the incoming radiation.

In this way, the determination is really a direct measurement of the intensity of the radiation, unlike the previous technique which was directed toward measuring the relative delay $\delta$ between two components of polarized visible light, which required evaluation of the interference order.

The object of the present invention is a device for non-destructive testing of the internal stress state of heat tempered plate glass, involving: a source of monochromatic infrared radiation which emits said radiation along an optic axis; an infrared light sensor placed on said optic axis; first optical concentration meas to concentrate the radiation emitted from said source on a point of a glass plate, situated on said optic axis; first optical polarization means to polarize in a polarization plane, the radiation being emitted from said source and concentrated on said point of the glass plate by said first concentration device; second optical concentration means to concentrate the radiation coming out from said point, after having passed through the glass plate, on said infrared radiation intensity detector; second optical polarization means to polarize said radiation coming from said point and concentrated on said detector by said second concentration device, is a polarization plane rotated 90° with respect to said polarization plane of the incoming polarized radiation; comparator means to compare a signal indicating the intensity of the radiation received from said detector with a determined threshold signal; and signalization means to signal when said intensity is greater or less than said pre-established threshold value.

It should be noted that the present invention uses a wave length longer than that used in previous techniques, to substantially modify the spectral interval of radiation, so that direct instrumental measurment of the delay value δ represents the stress state.

In particular, the use of invisible infrared radiation (for example, near infrared of 1.5 μ) makes it unnecessary to count the interference fringe since it shifts the maximum practical limit of measurable stress from approximately 40 mPa to approximately 100 mPa for a 3 mm thick plate.

The advantages arising from this system are several:

Elimination of the need to evaluate the interference order;

Conseguent elimination of the subjectivity of this evaluation;

Automation of the measurement;

Use of monochromatic infrared sources of low energy expenditure eg., an (LED);

Improved resolution due to the use of monochromatic sources;

Use of standard components;

Less dependence on electromagnetic radiation disturbances in the environment, the only remaining source of this radiation being incandescent lights, although to a limited degree.

DETAILED DESCRIPTION OF THE INVENTION

The present invention will be described below in one of its preferred embodiments, with reference to the attached drawings, in which.

Figure 1:
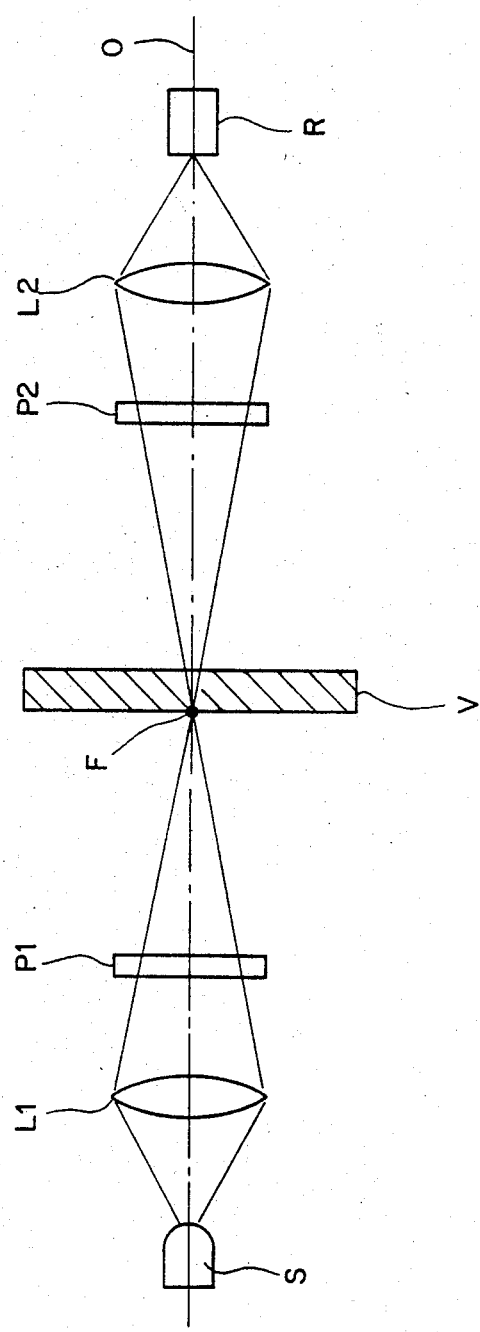
FIG. 1 shows an optical scheme of the device according to the invention.

As shown in FIG. 1, the apparatus for measuring the stress in the edge of a heat tempered glass plate consists of a source of infrared radiation S which emits infrared radiation in the direction of the optical axis O. The radiation is collected by a lens L1 and converged toward a point F on a glass plate V, placed on the optical axis O and on the focal plane of the lens L1. An infrared polarizer P1 ensures that the incident radiation on point F is polarized in a certain plane. After passing through the thickness of the plate V, the radiation is collected by a lens L2 and made to converge on an infrared sensor R. The radiation beam is passed through an infrared polarizer P2 which polarizes it in a plane rotated 90° with respect to polarizer 1.

As shown, the glass plate sample V is placed in focal area common to both lenses L1 and L2. Obviously, collimators may be used instead of lenses to increase the precision of the measurement.

The suitably amplified electrical signal from the sensor R is compared electronically with a prefixed value which represents the minimum experimental value for acceptable edge stresses. This comparation and threshold calibration may be performed by known methods, with standard electronic components.

Figure 2:
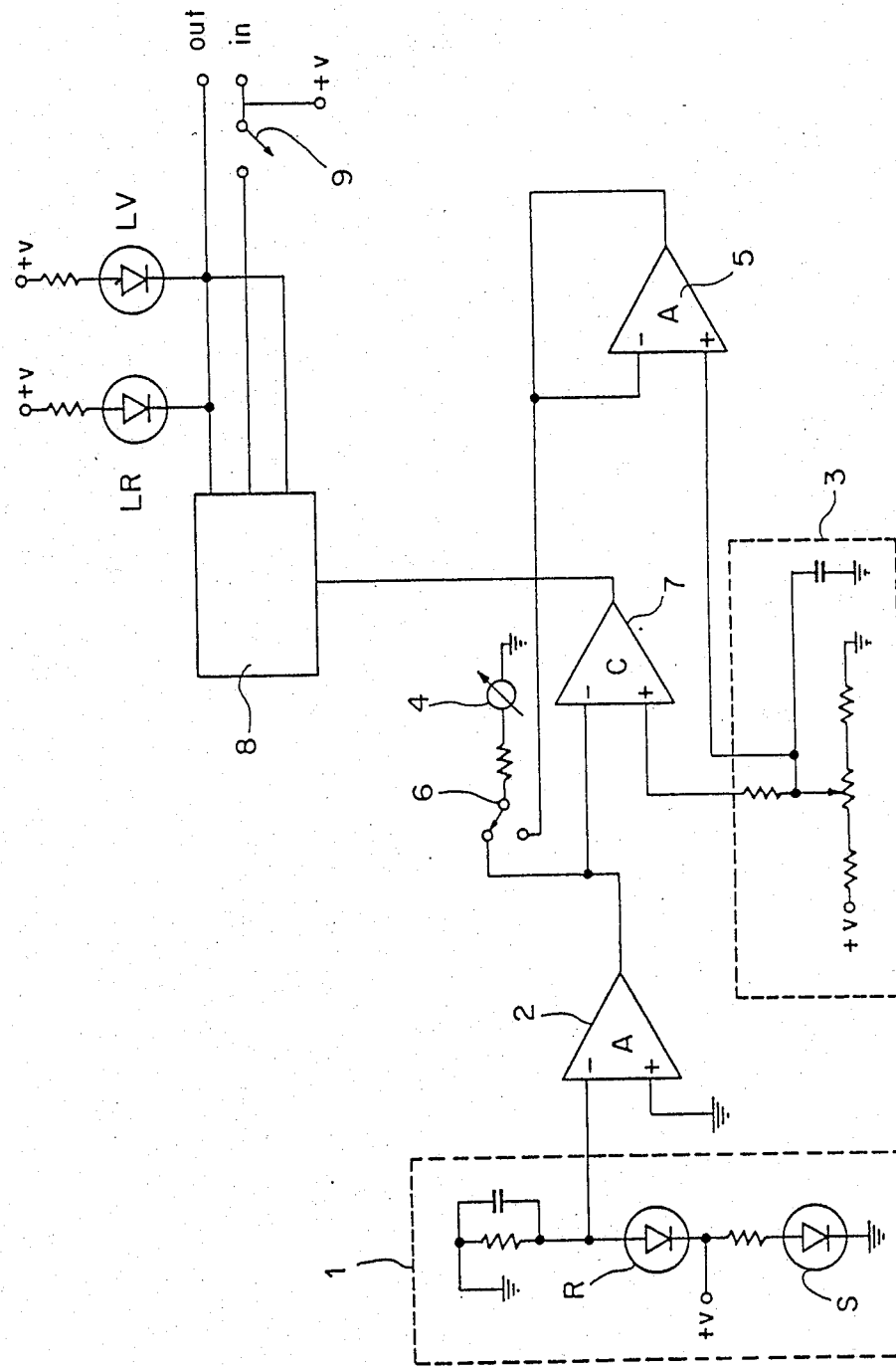
FIG. 2 shows a scheme of the circuit for processing and utilizing the signals obtained from a device as shown in FIG. 1.

FIG. 2 shows an example of the realization of an electronic system which processes and utilizes the signals obtained with the device in FIG. 1.

FIG. 2 shows a differentiator group in which the electrical signal from sensor R is differentiated to be sent to an ampilifier 2.

A circuit for generating the threshold signals is indicted with 3. The threshold signal may be controlled by means of an instrument 4 after having been amplified in an amplifier 5, and the circuit of the instrument 4 may also be used to control the signal emanating from the differentiator 1, by means of switching a switch 6.

The threshold signal prefixed by means of the circuit from threshold generator 3 is compared with the signal from the amplifier 2 by means of a comparator circuit 7 which transmits to a logic state detected, on the basic of a comparison of said two signals.

The logical circuit 8 signals the state determined and activates signalizing devices which signal whether the stress state of the glass plate being tested is within the prescribed limits. For example, the signalizing devices may consist of red light (LR) or green light (LV) LED which lights up to signal approval or rejection of the test plate. The OUT terminal is indicated as a terminal to measure the signal in case it is eventually used, and the IN terminal indicates a terminal which permits, by means of switch 9, the apparatus to be placed in operation when a glass plate to be tested is introduced in it.

The light source S and the sensor R may also consist of infrared active LED, with the result that the entire system is very simple to manufacture and very reliable to operate.

While a preferred embodiment of the invention has been described, it may of course be realized differently using known technologies, without going beyond the bounds of the present invention.

We claim:

1. Device for the non-desctructive testing of the internal stress state of heat tempered plate glass including: a sample comprising heat tempered plate glass; a source of monochromatic near infrared radiation for emitting near infrared radiation along an optical axis; first optical concentration means on said optical axis for concentrating the incident radiation emitted from said source on a point of a heat tempered glass plate placed with its thickness along said optical axis; first optical polarization means, placed between said first concentration means and said point of the heat tempered glass plate, for polarizing the incident radiation coming from said first concentration means, in a first polarization plane; second optical polarization means for polarizing the incident radiation coming from said point on the heat tempered glass plate, in a second polarization plane rotated 90° with respect to said first polarization plane; second optical concentration means for receiving the radiation from said second polarization means; and an infrared light sensor for receiving the radiation coming from said second concentration means, comprising means for generating an electrical signal controlled by the intensity of the radiation; electronic comparator means for comparing said signal of the radiation intensity with a threshold signal; and signalization means for signaling whether said intensity is greater than or less than said threshold signal.

2. Device according to claim 1, in which said infrared radiation source is a light-emitting diode.

3. Device according to claim 1, in which said generating means is a photodiode.

4. Device according to claim 1, in which said comparator means comprises: a differentiator circuit for differentiating the output from said sensor and generating a differentiated signal; a threshold signal generator circuit; and a comparator circuit for comparing said differentiated signal and said threshold signal and generating logic state signals which indicate whether said differentiated signal is greater than or less than said threshold signal.

5. Device according to claim 4, in which said signalization means comprises a logic circuit for processing said logic state signal from the comparator and activating signalization devices.

6. The device of claim 1, wherein said sample has an internal stress state of about 40–100 mPa.

7. The device of claim 6, wherein said sample is about 3 mm thick.

8. A method for the non-destructive measuring of the internal stress state of heat tempered plate glass comprising:

transmitting polarized near infrared monochromatic radiation through a point area of said heat tempered plate glass;

cross-polarizing the radiation output from said plate glass;

converting the intensity of said non-polarized output radiation into an electric signal;

comparing said intensity signal with a prefixed threshold signal and obtaining a logic state signal; and producing a signalization signal, depending on the state of said logic state signal.

9. The method of claim 8, wherein said heat tempered plate glass has an internal stress state of about 40–100 mPa.

10. The method of claim 9, wherein said heat tempered plate glass is about 3 mm thick.

* * * * *